United States Patent [19]
Leigh

[11] Patent Number: 4,667,684
[45] Date of Patent: May 26, 1987

[54] BIOPSY DEVICE

[75] Inventor: Harold G. Leigh, St. Louis County, Mo.

[73] Assignee: Bio-Medical Resources, Inc., St. Louis, Mo.

[21] Appl. No.: 699,805

[22] Filed: Feb. 8, 1985

[51] Int. Cl.⁴ ............................................. A61B 10/00
[52] U.S. Cl. .................................... 128/754; 128/305; 604/157; 604/164
[58] Field of Search .................................. 128/749–759, 128/305; 604/157, 156, 164–165, 171, 161, 117

[56] References Cited

U.S. PATENT DOCUMENTS

| | | | |
|---|---|---|---|
| 3,608,544 | 9/1971 | Schnepper | 128/751 |
| 3,913,584 | 10/1975 | Walchle et al. | 604/164 X |
| 3,989,033 | 11/1976 | Halpern et al. | 128/754 |
| 4,282,884 | 8/1981 | Boebel | 128/751 |
| 4,378,810 | 4/1983 | Ishizaki et al. | 128/754 |
| 4,402,683 | 9/1983 | Kopman | 604/175 |
| 4,411,653 | 10/1983 | Razi | 604/157 |
| 4,445,517 | 5/1984 | Feild | 128/752 |
| 4,461,305 | 7/1984 | Cibley | 128/751 X |
| 4,559,041 | 12/1985 | Razi | 604/164 X |

FOREIGN PATENT DOCUMENTS 0683726 9/1979 U.S.S.R. .............................. 128/755

Primary Examiner—Kyle L. Howell
Assistant Examiner—Angela D. Sykes
Attorney, Agent, or Firm—Paul M. Denk

[57] ABSTRACT

A biopsy device for single-handed usage by the medical practitioner for obtaining a specimen of suspected tissue, incorporating a stylet reciprocably movable within a cannula, both the stylet and cannula being fixed at their ends to respective hubs, both hubs being located within a guideway provided within the upper segment of a pistol grip style of hand gripping device, wherein the upper end of its trigger mechanism being operatively associated with the first hub and upon its depressing urging said cannula forwardly of the device, whereby upon initial urging of the device into a suspected portion of the patient's body, and urging the second hub and stylet forwardly thereof, then depressing and holding the trigger mechanism, and withdrawing of the device from the patient, a biopsy specimen is obtained for analysis.

14 Claims, 19 Drawing Figures

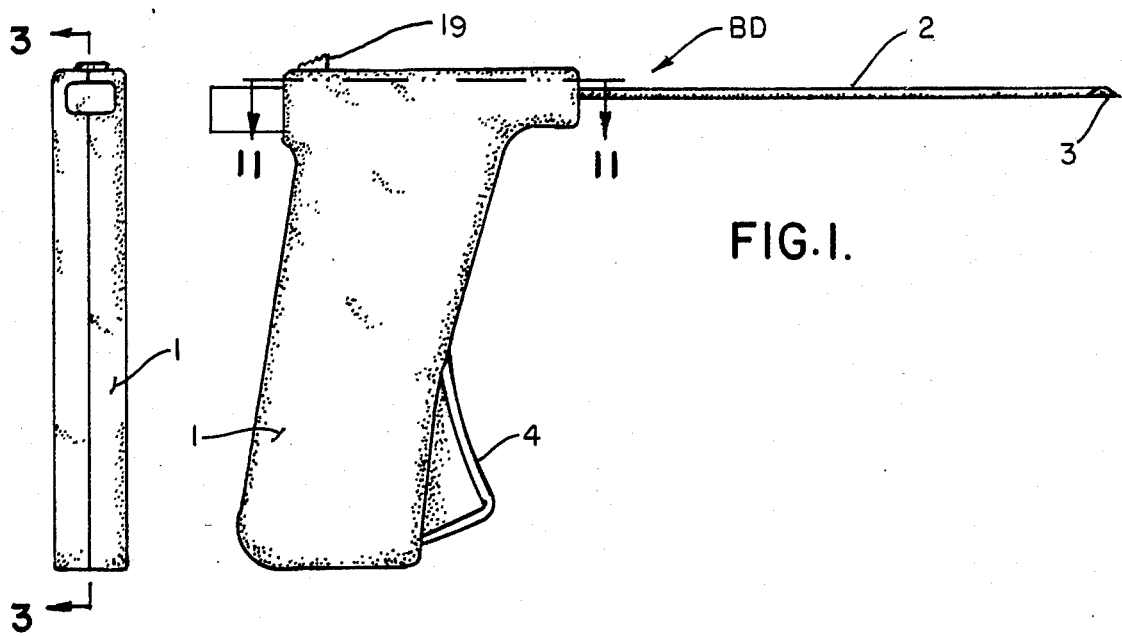
FIG.1.
FIG.2.
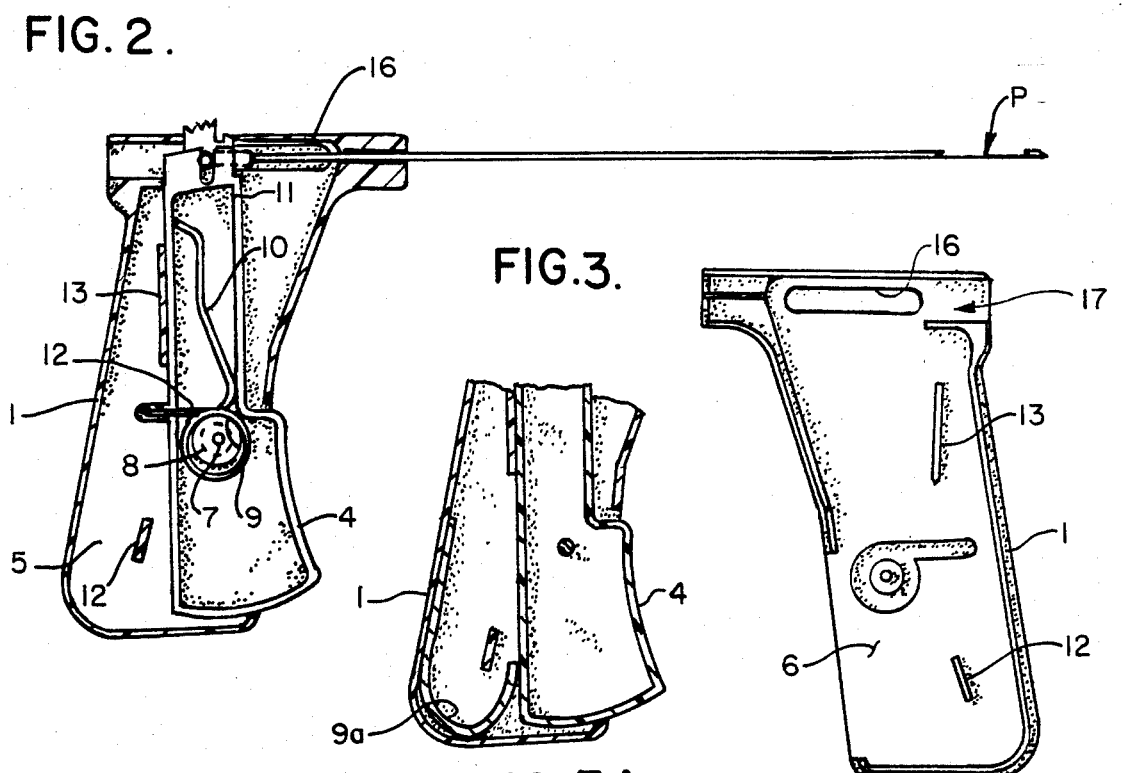
FIG.3.
FIG.3A.
FIG.4.
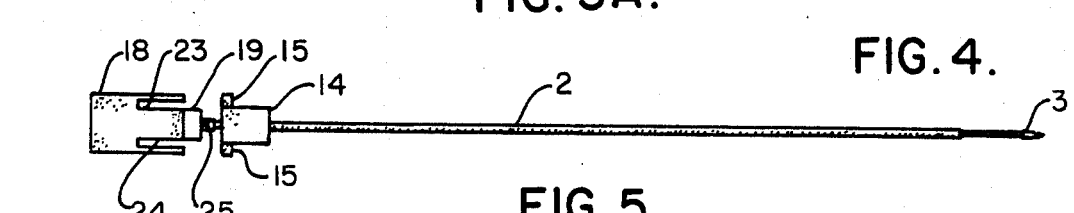
FIG.5.

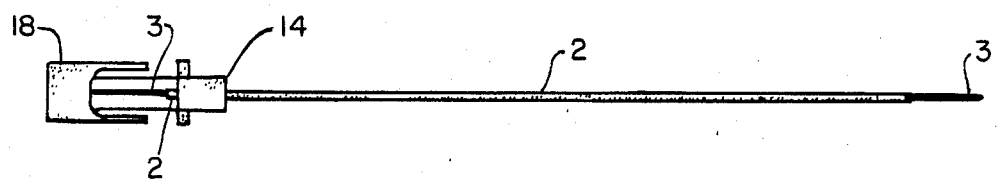
FIG. 6.
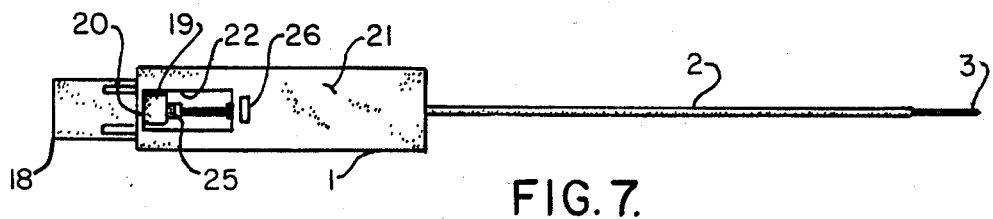
FIG. 7.
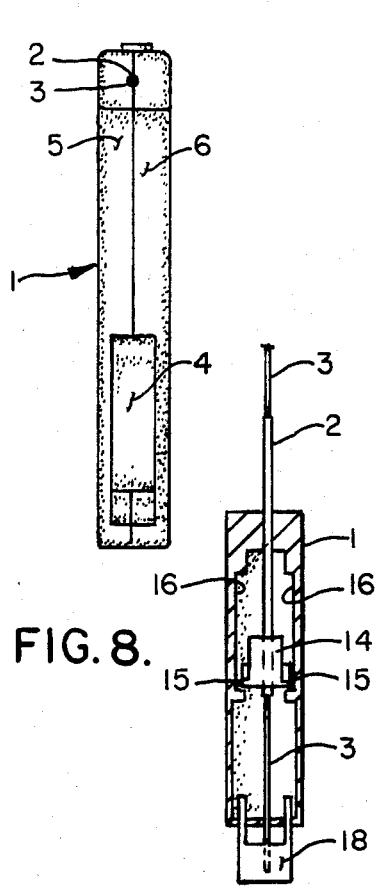
FIG. 8.
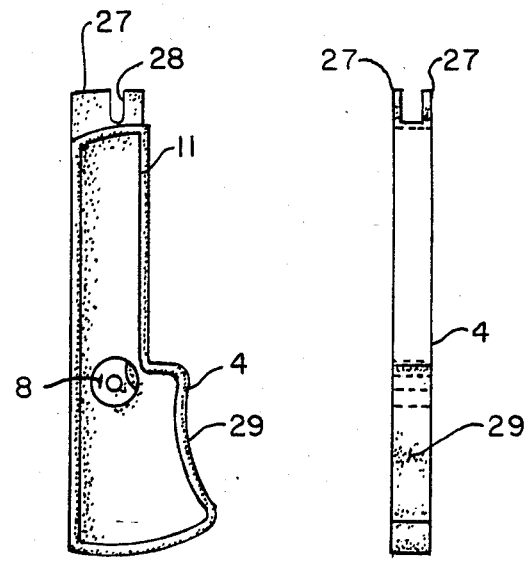
FIG. 9.
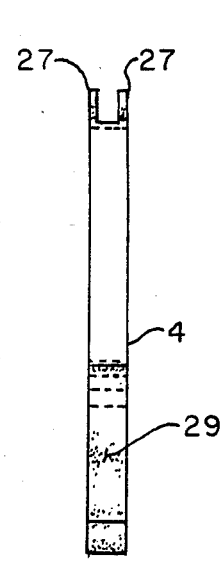
FIG. 10.
FIG. 11.
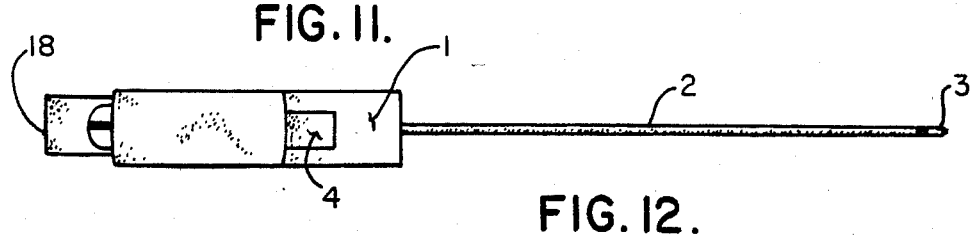
FIG. 12.

BIOPSY DEVICE

BACKGROUND OF THE INVENTION

This invention relates generally to a biopsy device, and more specifically pertains to a biopsy device that can be single-handedly deployed by the medical practioner in obtaining a specimen from a suspect diseased area of a patient.

There are a variety of biopsy instruments that have been long available upon the market. For example, the patent to Griffith, U.S. Pat. No. 3,477,423, discloses one such biopsy instrument, which is of the finger manipu- -lating type, and while this particular device apparently has been rather effective for achieving its intended purposes over the years, one of the advantages of applicant's new style of biopsy instrument is the addition of the substantial sized pistol grip structure that mounts the stylet and cannula for attaining all of their cooperating functions while obtaining a biopsy.

Various styles of instruments that incorporate handle means in cooperation with their operating components have been available in the art, such as the cutting instrument disclosed in the U.S. Pat. No. 2,710,000. In addition, the rotary punch mechanism for obtaining biopsy specimens shows a similar type of device, incorporating a pistol grip type of means, for triggering its spring-powered instrument, as shown in the U.S. Pat. No. 3,692,020. A conization instrument for obtaining cervical canal biopsy specimens is shown in the U.S. Pat. No. 3,613,662. A device for ligating suturing, and dividing organic tubular structures is shown in the instrument of U.S. Pat. No. 3,675,688. Furthermore, a device for draining the eardrum is shown in the U.S. Pat. No. 3,888,258, and which incorporates a trigger mechanism for initiating its operations. Likewise, a three-stage surgical instrument for controlling the operations of stapling during suturing is shown in the U.S. Pat. No. 3,955,581. Another biopsy device, having a trigger mechanism, is shown in the patent to Halpern, U.S. Pat. No. 3,989,033, and this particular device, while incorporating a pistol grip holding means, is just structured entirely differently from the device of applicant, for attaining, what it describes, as the guillotine derived specimen. An apparatus for spaying large animals, incorporating trigger means, is shown in the U.S. Pat. No. 4,220,155. Another old style biopsy device, incorporating a pair of tongs, is shown in the patent to Utsching, U.S. Pat. No. 901,567. A tonsilotome, for apparently performing tonsillectomy, is shown in the patent to Richter, U.S. Pat. No. 614,760. Another biopsy needle device, for providing relative functioning between its needle and sheath is shown in the patent to Silverman, U.S. Pat. No. 705,949. Another Silverman patent, disclosing a biopsy device, is shown in the U.S. Pat. No. 3,001,522. Stewart U.S. Pat. No. 3,175,554, shows a split biopsy needle mechanism. The French Pat. No. 1,267,960, shows another variation upon the cooperation between the needle, and its sheath, for obtaining a biopsy specimen. In addition, the German Pat. No. 142,879, shows another form of biopsy obtaining device.

There are still a variety of other U.S. patents disclosing instruments for use in performing particular medical diagnostic functions. For example, an adenotome is disclosed in U.S. Pat. No. 1,339,692. A diagnostic needle is shown in the patent to Muir, U.S. Pat. No. 1,585,934. The Hoffman patent discloses a needle, or device, for obtaining biopsy specimens, in its U.S. Pat. No. 1,867,624. And, the Turkel patent discloses a biopsy needle in U.S. Pat. No. 2,496,111.

In view of the foregoing, it can be seen that the art is replete with various types of medical instruments, even of the biopsy type, that are useful for performing particular medical diagnostic functions, but the structure of applicant's device, the manner in which it is assembled, and the method by which it is used, affords a rather substantially stable biopsy device that can be operated by the medical practioner single-handedly, thereby freeing the practitioner to use his other hand for obtaining proper guidance, a convenient hold upon the patient, all while obtaining the needed biopsy specimen for medical diagnosis.

It is, therefore, the principal object of this invention, to provide a particular style of tissue cutting device that allows the physician or attending surgeon to be able to promptly and successfully obtain a biopsy from the patient, for the purpose of obtaining that tissue sample as needed for further analysis to confirm the presence, or not, of diseased tissue.

Another object of this invention is to provide a truly one-handed biopsy device that permits the physician to conveniently and quickly obtain a biopsy specimen with reasonable precision.

A further object of this invention is to incorporate the pistol grip style of hand gripping means into the construction of a biopsy device, so as to provide it with substantial size and structural integrity to assure the proper placement and extracting of a specimen tissue for analysis.

Another object of this invention is to provide a biopsy device that is sterile, and perhaps single patient use disposable, thus eliminating any possibility of cross-contamination between patients, or, as a single use device, of locations upon the same patient.

Still another object of this invention is to provide to a cannula hub slide mechanism contained within the housing of a biopsy device, and more specifically within its hand gripping means, and which device can be used either with the left hand or the right hand as desired.

Another object of this invention is to provide a biopsy device wherein its stylet is easily removable thus permitting the doctor to make multiple passes without removal of the cannula from the instrument. For example, in many of the current biopsy devices available, they are of such delicate size, and construction, that the physician frequently looses his orientation while inserting and performing the biopsy procedure. There is little firmness provided in a biopsy instrument that simply utilizes finger gripping means for providing both direction and guidance to the instrument during its application.

Another object of this invention is to provide a biopsy device that can be quickly operated and perform all of the essential steps necessary to obtain a precise specimen for medical diagnosis.

Still another object of this invention is to provide a housing for a biopsy device, that incorporates both a handgripping means, and its trigger mechanism, furnishing the physician with a device of substantial structural integrity that it can be manipulated rather precisely single-handedly for obtaining a specimen for analysis.

Another object of this invention is to provide a biopsy device wherein its trigger mechanism is spring loaded to provide for its immediate return to its normal position after withdrawal of the stylet and its cannula from within the patient.

These and other objects will become more apparent to those skilled in the art upon reviewing the summary of this invention, and upon undertaking a study of the description of its preferred embodiment, in view of the drawings.

SUMMARY OF THE INVENTION

This invention is generally developed incorporating a pistol grip style of component, which not only can be single-handedly manipulated during usage, but all of the other operational procedures required to satisfactorily obtain a tissue biopsy can be achieved with one hand. The device, being a one-handed device, permits the physician to utilize his free hand for steadying the patient or for performing another incidental maneuver that may be required during performance of a biopsy function. Such a pistol grip gives the user excellent control during the performance of the procedure, and which is very necessary during the undertaking of this particular medical maneuver.

The manner in which the device of this invention is constructed, and packaged, provides a sterile, single use, type biopsy instrument, and therefore, eliminates the possibility of any cross contamination of patients. Furthermore, the device is disposable, and therefore, eliminates any possibility of disease transmission. Furthermore, since the various operating components, such as the integral slide mechanism that houses and guides the cooperation between reciprocal movement of the stylet, and its cannula, for this device are housed within a handle means, it may be utilized either by the left or right handed physician without any conversion to its structure before application. The cannula is always orientated properly in relationship to its encase stylet. In this manner, this arrangement prohibits any rotation of the cannula, with respect to the stylet, either before, during, or even following usage, and therefore, provides a restricted pathway in both its forward and reverse movements. The housing for this device, and its trigger stop mechanism, which is used for limitation of the cannula stroke, allows only the proper measured movement forwardly, and also in the backward or reverse direction, in order to prevent any accidental or inadvertent excessive, or less, penetration by the stylet when inserted into the patient's body.

This particular biopsy device also features within its construction a movable stylet which thus permits the physician to make multiple passes without removing the cannula by utilizing the same pathway, that is, its sheathing cannula structure. Since the cannula hub for this invention is so easily controlled by its trigger mechanism, and is inter related in its component structure for furnishing its inherent functioning, and since the stylet may be advanced rather quickly through maneuvering of the operator's thumb, the whole procedure can be rapidly and expeditiously performed, with a minimum of time and discomfort experienced by the patient. Obviously, speed is of the prime concern when the physician performs such a biopsy procedure.

The housing means for this particular biopsy device orients that cannula hub and thus eliminates both lateral and vertical movements or shifting between these components, during their installation, and application. The stylet hub is designed to be maintained in communication with the housing handle, the stylet is within the cannula, and there is always that proper alignment for functioning between these two components so that when a biopsy or soft tissue specimen is taken, the physician has the assurance that the procedure is always being performed correctly and in a uniform manner.

In addition to the foregoing, the linkage connection between the forward movement given to the cannula and its enclosed stylet, through the generation of finger force upon the trigger mechanism for this particular invention, is such that significant force may be generated which permits the cannula to cut through even the very dense and toughest of tissue, should a tissue specimen or biopsy be required from such an area of the body. The spring loading of the mechanism, through a simple release of said trigger, simply forces the trigger mechanism to its static position, which allows the cannula to return to its natural position, thereby allowing the notch or pocket on the stylet to become immediately exposed for a quick removal of the obtained specimen. The catch means on the stylet structure prevents the stylet hub from being forced into a forward or backward motion when the cannula is being moved forward through any tough tissue. In addition, this latching means also helps to limit the stylet hub movement forwardly beyond that which is required.

The various parts for the left and right hand handle forming members, which form the pistol grip design for this particular invention, when it is held properly by the operator, is in reasonably close proximity to the patient, and acts as a cannula guide preventing lateral and/or vertical movement or shifting of the cannula during its manipulation when obtaining a tissue biopsy sample.

The foregoing provides a brief but general overview of the advantages and improvements that can be derived from the soft tissue cutting device of this particular design.

BRIEF DESCRIPTION OF THE DRAWINGS

In referring to the drawings, FIG. 1 discloses a right side view of the biopsy device of this invention;

FIG. 2 is a back view thereof;

FIG. 3 is an internal sectional view of the hand gripping means of this invention, taken along the line 3—3 of FIG. 2;

FIG. 3A is an internal sectional view of the hand gripping means of this invention, showing an alternative spring means for use in conjunction with the trigger mechanism;

FIG. 4 is an interior view of the right side of the hand gripping means, as removed from covering the remaining hand gripping portion as previously disclosed in FIG. 3;

FIG. 5 is a top view of the first and second hub means of this invention having their respective cannula and stylets secured thereto, with the stylet disclosed slidingly inserted within the said cannula;

FIG. 6 is a similar view to that of FIG. 5, with a top portion of the second hub being removed to disclose that the stylet secures rigidly at one end into the hub body;

FIG. 7 discloses a top view of the biopsy device;

FIG. 8 is a front view of the biopsy device;

FIG. 9 is a side view of the trigger mechanism of the biopsy device;

FIG. 10 is a front view thereof;

FIG. 11 is a sectional view taken along the line 11—11 of FIG. 1;

FIG. 12 is a bottom view of the biopsy device;

DESCRIPTION OF THE PREFERRED EMBODIMENT

Figure 13:
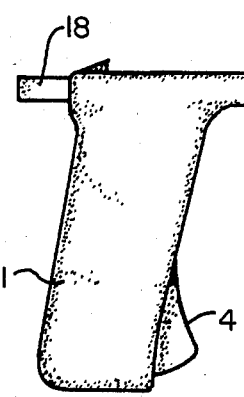
FIG. 13 is a side schematic view of the biopsy device when readied for application for taking a tissue specimen.
Figure 14:
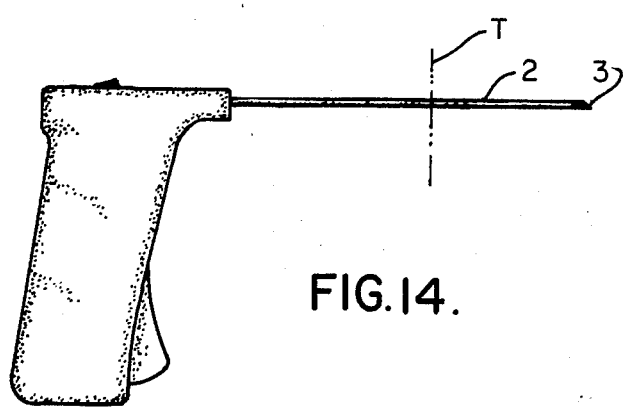
FIG. 14 is a side schematic view of the second step during application of the biopsy device, showing the device in the process of piercing the skin or tissue surface.
Figure 15:
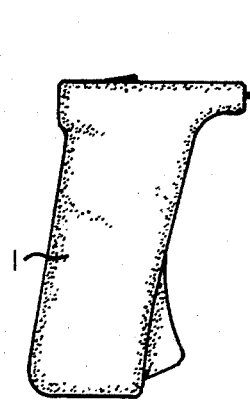
FIG. 15 is a side schematic view of the biopsy device with the stylet hub advanced forwardly for exposing the stylet biopsy containing pocket.
Figure 16:
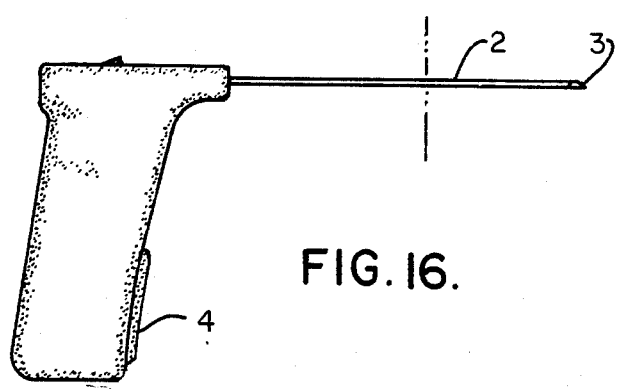
FIG. 16 is a side schematic view of the biopsy device with its trigger mechanism depressed for closing the cannula over the stylet pocket containing biopsy specimen.

In referring to the drawings, and in particular FIGS. 1, 2, 7, 8, and 12, the biopsy device BD of this invention is generally disclosed. The device incorporates a hand gripping means 1 generally fabricated to the configuration of a pistol grip style of hand holding means. As can be seen, projecting forwardly from the hand gripping means is the cannula 2 for the invention, and having projected even further forwardly of it is the stylet 3. The function of the cannula, and the stylet, and their use in obtaining a biopsy from a patient under analysis is quite readily explained in the prior art, such as that previously alluded to. In addition, extending some distance forwardly of the front of the hand gripping means 1 is the trigger mechanism 4, which is pivotally mounted generally within the said gripping means 1.

In referring further to FIGS. 3 through 7, the internal mechanisms for this biopsy device are disclosed. As can be seen, the hand gripping means 1 forms a housing that is fabricated from two molded components 5 and 6, which when brought into complimentary contact, provide complete enclosure for the fabricated handle. Contained within the hand gripping means, and operatively associated with at least the left side segment 5, is the trigger mechanism 4, being pivotally mounted upon a pin 7 as firmly fixed to the interior of the handle or housing segment 5. In addition, the trigger mechanism includes an integral boss 8, which slides over the pin 7, and mounted upon the boss 8 is the spring means 9, incorporating a pair of legs, such as the leg 10 that extends upwardly within the trigger mechanism and which constantly biases its upper segment, as at 11, rearwardly within the handle means. Another leg 12 of the spring means is fixed within a slot formed upon the interior of the handle segment 5, as can be seen, so as to provide for a continuous stress upon the spring 9, which constantly urges, as previously explained, the upper segment 11 of the trigger mechanism rearwardly, therefore providing for a normally exposed forwardly extending portion of the said trigger mechanism 4 exteriorly of the hand gripping means or housing 5. When the trigger mechanism 4 is depressed, as pivoted about the pin 7, it is limited in its rearward movement by means of the stop 12. In addition, the forward movement of the trigger mechanism 4 is generally limited by means of the stop 13, upon its contact by the rearward edge of the upper segment 11 of the said mechanism, as can be seen in FIG. 3.

FIG. 3A discloses an alternative embodiment for furnishing the spring means for functioning of the trigger mechanism of this invention. As can be seen, the spring means 9A is constructed more in the nature of an arcuately shaped leaf spring, and which biases against the back edge of the hand gripping means 1, as can be seen, while the opposite end of the said spring biases against the back side of the trigger mechanism 4. In this manner, the spring means functions quite similarly to the spring means previously analyzed with respect to FIG. 3. In addition, a related but smaller type of spring means 9A may be used in lieu of that disclosed in FIG. 3A, by locating it in the upper front portion of the hand gripping means, so that it biases against the front of said means, while at the same time contacting the front of the trigger mechanism 4, at that location, for urging it constantly it into its released configuration, as disclosed in said drawing FIGS. 3 and 3A.

The various structures utilized to provide for the regulated reciprocal movements for the stylet 3, and the cannula 2, include a first hub 14, and which has fixed to it the back end of the cannula 2. The hub includes a pair of trunnions 15, one extending to either of its sides, and these trunnions are designed for locating within the respective slots 16 formed in either side of the handle or hand gripping means 1, and more specifically within its segments 5 and 6.

The upper end of the hand gripping means is configured to generally form a guideway, as at 17, along the length of the upper end of said means, and in conjunction with the slot 16, provide the structural means for positioning and properly guiding the reciprocal movements given to the cannula or sheath 2, in addition to the sylet 3, during their independent shifting while a biopsy is performed. The stylet 3, and more specifically at its rearward end, is rigidly mounted into a second hub 18, and as can be seen, since the stylet 3 extends through the cannula 2, these hubs cooperate with each other to maintain alignment of these components, within the upper segment of the hand gripping member 1, or its housing, during usage of the biopsy device. Thus, during installation, the first hub 14, and more particularly its trunnions 15, are maintained within the guide slots 16, as shown, while the second hub 18 is arranged within the guideway 17, each of these hubs being arranged for longitudinal reciprocation within their respective areas. And, as previously explained, since the cannula 2 surrounds the stylet 3 for a substantial distance, these components are reasonably fixed for very stable longitudinal reciprocation within the upper segment of the hand gripping means 1, without any possibility of their turning.

As can also be seen in FIG. 7, in addition to FIG. 5, the hub 18 has a forwardly extending latch 19, and which latch is designed to encounter the back structure or stop 20 formed of the top surface 21 of the hand gripping means 1. Thus, this limits the rearward movement to the hub 18, in addition to the cannula 2 fixed therewith. In addition, as can be seen in FIG. 1, this latch 19 extends upwardly through the opening 22 formed through the upper surface 21 of the housing, and therefore is disposed for contact and engagement with that stop means 20, as previously defined. The top of the latch 19 may be serrated as noted, to facilitate it gripping by the finger during manipulation. On the other hand, as can be further seen in FIG. 5, a pair of slots as at 23 and 24 extend laterally of the latch 19, within the second hub 18, and therefore the latch has a degree of resiliency built into it, so that a depressing of it downwardly within the opening 22 will allow it to bypass the structural stop means 20, and provide for a total removal of the second hub 18, and its stylet 3, from the biopsy device, if necessary. This can be performed where multiple passes may be made of the biopsy device, but it may be desired, in each instance, to utilize a new stylet with the administering of each pass by the medical practitioner in obtaining a specimen.

In addition to the foregoing, it can be seen that a detent means 25 extends further forwardly of the latch 19, is likewise resilient in its structure, and it is designed to provide for engagement within the aperture 26, formed through the top surface 21 of the housing 1, as when the hub 18 may be moved to its forwardmost position. When the detent is arranged within the aperture 26, the hub then will be fixed in place, thereby locating the stylet 3 within a reasonably permanent position within the device, until such time as the latch 19 may be depressed, thereby allowing for a disengagement of the detent 25, and further allowing, once again, a predetermined rearward movement to the hub 18.

The more specific construction of the trigger mechanism 4 is also shown in FIGS. 9 and 10, and it can be seen that extending integrally and further upwardly from its upper segment 11 is a bifurcated guideways 27, each having a slot 28 formed therein, and the trunnions 15 of the first hub 14 being designed for seating within these slots 28. Hence, upon actuation of the trigger mechanism 4, as by depressing of a finger upon its exposed arcuate surface 29, the guideways 27 urge the hub means 14 either forwardly or rearwardly depending upon the direction of its pivot. Thus, it can be seen that the longitudinal shifting of the hub 14, and its fixed cannula 3, can be achieved independently through a manipulation of the trigger mechanism 4. On the other hand, the second hub 18, and its fixed stylet 3 can also attain independent longitudinal shifting forwardly or rearwardly within the upper segment of the hand gripping means 1, simply through a manual force exerted upon the said second hub 18.

Figure 18:
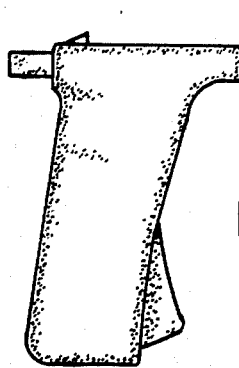
FIG. 18 is a side schematic view of the biopsy device with its cannula hub extended rearwardly in preparation for another pass into the patient for obtaining a biopsy for analysis.
Figure 17:
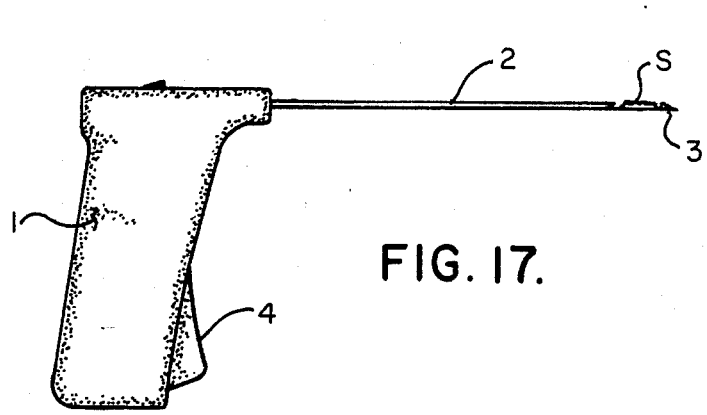
FIG. 17 is a side schematic view of the biopsy device after withdrawal from the body of the patient, and its trigger mechanism released, for revealing the biopsy specimen within the stylet pocket.

In operation, and during usage of this biopsy device by the practitioner, and in referring to FIGS. 13 through 18, FIG. 13 discloses the device 1 with its hub 18 fully retracted, and its trigger mechanism 4 untouched, and in its static condition extending forwardly, at its downward end, of the housing 1, and in such condition, the first hub 14 also will be fully retracted. Hence, both the cannula 2 and its stylet 3 will be fully retracted, the stylet being almost completely enclosed within said cannula. Under this condition, the medical practitioner grips the handle 1 and inserts by piercing the cannula and its stylet through the patient's tissue, illustrated as at T. See FIG. 14. Following this, and referring to FIG. 15, the practitioner then forces by thumb pressure the second hub 18 forwardly of the device, and when this occurs, the stylet 3 and more specifically its pocket P becomes fully exposed within the suspect tissue at its situs within the patient's body. At this point, the hub 18 is fully extended forwardly within the guideway 17, and its detent 25 locates within the aperture 26 provided through the upper surface 21 of the housing, thereby locking this hub, and the stylet, into position. Following this, and referring to FIG. 16, the trigger mechanism 4 is depressed, as through the exertion of a squeeze by the hand of the practitioner conducting the test, and when this occurs, the first hub 14 is urged forwardly of its guideway slots 16, to its fullest extent, and under this condition its attached sheath 2 overrides the stylet 3, in its now specimen or biopsy containing pocket P, therefore encapsulating the specimen therein. When this happens, and while the practitioner continues to hold the trigger mechanism 4, he pulls the device from the patient's body, releases the trigger mechanism 4, thereby exposing the biopsy or specimen S taken by the stylet 3. This is disclosed in FIG. 17. Then, the detent means 25 can be disengaged from its retaining aperture 26, and the second hub 18 pulled into a rearward movement, retracting, once again, the stylet 3 within the cannula 2, as can be seen in FIG. 18. Thus, under this condition, the biopsy device is ready for reuse and for another pass upon the same patient by the practitioner, if necessary, or in addition, if it is desired to take a biopsy from another portion of the patient's body, and to avoid some degree of contamination, the latch 19 can be depressed, or lowered, for bypassing the stop 20, and the entire hub 18 with the stylet 3 can be removed and disposed of. After this, another and replacement, in addition to sterile, hub 18 and new stylet or needle 3 can be reinserted into the apparatus and readied for reuse, in the position as shown in said FIGS. 13 and FIG. 18.

It should be commented, upon reviewing the invention herein, and its operation, that the entire apparatus, or more specifically its hand gripping means or housing 1 can be molded from a plastic, inexpensively, with the stylet 3 and its cannula 2 being usually formed of stainless steel. But, even under these conditions, the entire apparatus can be made disposable.

Variations or modifications to the subject matter of this invention may occur to those skilled in the art upon reviewing the disclosure herein. Such modifications or changes if within the spirit of this invention are intended to be encompassed within the scope of any claims to patent protection issuing upon this invention. The description of the various components made within this disclosure, and their illustration within the drawings, are set forth principally for illustrative purposes only.

Having thus described the invention what is claimed and desired to be secured by letters patent is:

1. A biopsy device for single-handed usage by the medical practitioner for obtaining a specimen of suspected tissue in a flesh piercing stylet or its integral pocket in cooperation with its reciprocal movement within a cannula, the improvement which comprises, a hand grip of substantial size and structural integrity in the form of a pistol grip supporting the stylet and cannula for single-handed usage, said hand grip having a front edge facing forwardly and a back edge facing rearwardly, and said hand grip having upper and lower edges, said hand grip incorporating a trigger mechanism pivotally mounted therein, said trigger mechanism extending substantially the length of the hand grip, a portion of said trigger mechanism extending exteriorly of the hand grip and forwardly thereof and capable of being selectively manipulated independently of the movement of the hand grip by the hand of the practitioner during application, said hand grip proximate its upper edge having a guideway therein, said cannula having a back end, a first hub fixing the proximate back end of the cannula thereto and mounted for sliding movement within said guideway, said stylet having a back end, a second hub mounting the back end of the stylet thereto and arranged for sliding movement also within the guideway and positioned rearwardly of the said first hub, said first hub and its affixed cannula disposed for sliding movement upon the stylet, said second hub having a portion extending rearwardly thereof and capable of extending from the back edge of the hand grip and disposed for being urged forwardly upon exertion of a hand force thereon, said trigger mechanism having an upper end, the upper end of the trigger mechanism operatively associated with the said first hub, whereby depressing of the said mechanism urges the said cannula forwardly of the device, and whereby upon initial urging of the device into a suspected portion of a patient's body, and urging the second hub and stylet forwardly thereof, then depressing and holding the trigger mechanism, and withdrawing of the device from the patient, a biopsy specimen is obtained for analysis.

2. The invention of claim 1 and including latch means operatively associated with the guideway and for preventing the second hub and its stylet from removal from the device when urged to a rearward position within the guideway.

3. The invention of claim 2 and wherein said hand grip has an opening in its top edge thereof, said latch means capable of being disposed forwardly within said opening, said hand grip having an aperture forwardly of its opening, said second hub having a detent formed extending forwardly thereof and disposed for engagement within said aperture thereby holding said second hub and its stylet in their forwardmost positions.

4. The invention of claim 3 and including a stop formed rearwardly of the hand grip, said second hub having the latch means extending upwardly thereof, said latch means engaging said stop to prevent further rearward movement of the said second hub.

5. The invention of claim 4 and wherein said latch means being resiliently formed of the second hub and upon its pressuring downwardly capable of by-passing said stop means for effecting removal of said second hub and the stylet from the biopsy device.

6. The invention of claim 5 and wherein a pair of slots are formed adjacent the latch means to provide its resiliency.

7. The invention of claim 1 and including spring means cooperating between said hand grip and the trigger mechanism for continuously biasing the upper end of said trigger mechanism and its first hub rearwardly of the guideway.

8. The invention of claim 7 and wherein said spring means incorporating a pair of legs, one leg of the spring means extending into the trigger mechanism, the second leg of the spring means being fixed to the interior of the hand grip.

9. The invention of claim 8 and wherein said hand grip has a cavity therein for disposition of said spring means.

10. The invention of claim 9 and including a pin provided through said cavity and whereby the trigger mechanism is pivotally mounted with respect to the hand grip.

11. The invention of claim 7 and wherein said spring means comprises a leaf spring biased between the hand grip and the trigger mechanism.

12. The invention of claim 1 and wherein said first hub has a pair of trunnions extending laterally therefrom and disposed within the guideway for directing the movement of the said first hub within the hand grip.

13. The invention of claim 1 and wherein said biopsy device is disposable.

14. In the method of obtaining a biopsy through single-handed application by the medical practitioner wherein a hub supported stylet incorporating a specimen pocket and cannula are incorporated with a pistol grip mounted trigger mechanism, comprising, aligning the cannula to substantially enclose the stylet, piercing said cannula and stylet into the suspected area of the patient, pushing the hub supported stylet forwardly to expose the stylet pocket to the tissue from which a speciment is sought, depressing the trigger mechanism for once again urging the hub supported cannula to slide over and enclose the stylet and its specimen, withdrawing the stylet and cannula from the patient while holding the trigger mechanism depressed, then releasing the trigger mechanism for withdrawal of the cannula from overlying the stylet pocket to expose the specimen for removal and for analysis.

* * * * *